(12) United States Patent
Zhou et al.

(10) Patent No.: US 11,026,990 B2
(45) Date of Patent: Jun. 8, 2021

(54) PUM 1 PROTEIN AS TARGET FOR VIRUS INHIBITION

(71) Applicant: Shenzhen International Institute for Biomedical Research, Shenzhen (CN)

(72) Inventors: Grace Zhou, Shenzhen (CN); Bernard Roizman, Shenzhen (CN); Yonghong Liu, Shenzhen (CN)

(73) Assignee: Shenzhen International Institute for Biomedical Research, Shenzhen (CN)

(*) Notice: Subject to any disclaimer, the term of this patent is extended or adjusted under 35 U.S.C. 154(b) by 0 days.

(21) Appl. No.: 16/477,406

(22) PCT Filed: Apr. 12, 2017

(86) PCT No.: PCT/CN2017/080213
§ 371 (c)(1),
(2) Date: Jul. 11, 2019

(87) PCT Pub. No.: WO2018/187957
PCT Pub. Date: Oct. 18, 2018

(65) Prior Publication Data
US 2020/0164020 A1      May 28, 2020

(51) Int. Cl.
*C12N 15/113*      (2010.01)
*A61K 38/02*       (2006.01)
*A61K 31/7088*     (2006.01)

(52) U.S. Cl.
CPC .......... *A61K 38/02* (2013.01); *A61K 31/7088* (2013.01); *C12N 15/113* (2013.01); *C12N 2310/11* (2013.01); *C12N 2310/14* (2013.01)

(58) Field of Classification Search
CPC .... A61K 38/02; A61K 31/7088; A61K 38/00; C12N 15/113; C12N 2310/11; C12N 2310/14; C12N 9/14; C12Y 306/04013; C07K 14/4702
See application file for complete search history.

(56) References Cited

U.S. PATENT DOCUMENTS

| 2004/0086945 A1 | 5/2004  | Sreekrishna et al. |
| 2005/0261217 A1 | 11/2005 | Dobie et al. |
| 2011/0059502 A1 | 3/2011  | Chalasani |
| 2011/0223616 A1 | 9/2011  | Atasoy et al. |
| 2017/0182182 A1* | 6/2017 | Seow ............ A61K 47/42 |

FOREIGN PATENT DOCUMENTS

| WO | WO-2011055311 | 5/2011  |
| WO | WO 2011/160052 | 12/2011 |
| WO | WO-2014105751 | 7/2014  |

OTHER PUBLICATIONS

International Search Report and Written Opinion for PCT/CN2017/080213 dated Jan. 8, 2018, 11 pages.
Kiani et al., "Repression of the Internal Ribosome Entry Site-dependent Translation of Hepatitis C Virus by an Engineered PUF Protein", Hepat Mon., No. 2, vol. 17, e45022, p. 1-9, 2017.
Narita et al., "A Novel Function of Human Pumilio Proteins in Cytoplasmic Sensing of Viral Infection", PLOS Pathogens, No. 10, vol. 10, e1004417, p. 1-11, 2014.
Bruns et al., LGP2 synergy with MDA5 in RLR-mediated RNA recognition and antiviral signaling, Cytokine 2015, 74, pp. 198-206.
Extended European Search Report for European Application No. 17905320.2 dated Jan. 14, 2021. 9 pages.
Fernandez et al., miR-340 inhibits tumor cell proliferation and induces apoptosis by targeting multiple negative regulators of p27 in non-small cell lung cancer, Oncogene 2015, 34, pp. 3240-3250.
Liu et al., PUM1 is a biphasic negative regulator of innate immunity genes by suppressing LGP2, PNAS Jul. 31, 2017, pp. E6902-E6911.
Yoneyama et al., Shared and unique functions of the DExD/H-box helicases RIG-I, MDA5, and LGP2 in antiviral innate immunity, The Journal of Immunology 2005, pp. 2851-2858, XP003018261.

* cited by examiner

*Primary Examiner* — J. E. Angell
(74) *Attorney, Agent, or Firm* — Sheppard Mullin Richter & Hampton LLP

(57) ABSTRACT

Disclosed is a method for prophylaxis or treatment of infection of a virus, or for modulating innate immunity, in a subject comprising administering to the subject a therapeutically effective amount of a PUM1 inhibitor. A pharmaceutical composition comprising the PUM1 inhibitor is also disclosed.

13 Claims, 5 Drawing Sheets
Specification includes a Sequence Listing.

PUM 1 PROTEIN AS TARGET FOR VIRUS INHIBITION

CROSS REFERENCE TO RELATED APPLICATION

The present application is a U.S. National Stage application under 35 U.S.C. § 371 of International Application No. PCT/CN2017/080213, filed Apr. 12, 2017.

SEQUENCE LISTING

The instant application contains a Sequence Listing which has been submitted in ASCII format via EFS-Web and is hereby incorporated by reference in its entirety. Said ASCII copy, created on Oct. 22, 2019, is named 44GC-297666-US-SL.txt and is 8,290 bytes in size.

TECHNICAL FIELD

The present invention is related, in one aspect, to a method for prophylaxis or treatment of infection of a virus in a subject, and in a further aspect, to a method for modulating cellular innate immunity. The instant invention also concerns pharmaceutical compositions for use in the methods and the use of a PUM1 inhibitor in the preparation of pharmaceutical compositions for prophylaxis or treatment of infection of a virus, or for modulating cellular innate immunity, in a subject.

BACKGROUND

Human cells express two pumillio proteins, PUM1 and PUM2. The primary function of PUM proteins described to date is that of post mRNA transcriptional regulators. Specifically both PUM1 and PUM2 contain a RNA sequence specific binding domain. In studies that detailed the consequences of the interaction, the results suggest that PUM proteins alter the function of the RNAs by altering their conformation. Other studies reported that PUM protein mediate translational silencing via a number of mechanisms. These include mRNA deadenylation, decapping, by blocking translation initiation or by facilitating their interaction with microRNAs. They have also been reported to be markers of stress granules in cells infected with Newcastle Disease Virus.

Pumilio was the first member of the PUF family of RNA binding proteins (RBPs) that are present in diverse species. PUF family members are readily identified by the presence of eight tandem copies of an imperfectly repeated 36 amino acid sequence motif called the PUM repeat and typically contain evolutionarily conserved sequences that are amino- and carboxy-terminal to the repeat region of the protein. The eight repeats, together with the terminal conserved sequences, form a sequence-specific RNA binding domain, the Pumilio homology domain (PUM-HD) that binds to the 3' UTR of the mRNA target.

BLAST search of the human EST division of the GenBank and the UniGene databases resulted in the identification of human Pumilio 1 which maps to chromosome 1p35.2 and Pumilio 2 maps to chromosome 2p13-24. Human Pumilio 1, also known as PUF or RBF, is expressed in the brain, heart, kidney, muscle, intestine, and stomach as well as in all fetal tissues and adult central and peripheral nervous system, cardiovascular, gastrointestinal, urogenital, hematopoetic and endocrine systems, and in cancer cell lines. DNA microarray studies have shown that Pumilio 1 is downregulated in squamous carcinoma cells as compared to UVB-irradiated human epidermal keratinocytes, associating changes in Pumilio expression with epithelial cancer.

Infectious agents like viruses have been and continue to be significant pathogens in humans and animals including high density farming animals such as pigs and poultry. There is a need to identify agents which can reduce infection and spread of these viruses and/or which ameliorate conditions caused thereby. Herpes viral infections, including herpes simplex virus type 1 (HSV-1) and type 2 (HSV-2) infections, are common infections worldwide. HSV-2 is the cause of most genital herpes and is generally sexually transmitted. In contrast, HSV-1 is usually transmitted via nonsexual contacts. Preexisting HSV-1 antibodies can alleviate clinical manifestations of subsequently acquired HSV-2. Furthermore, HSV-1 has become an important cause of genital herpes in some developed countries. Varicella Zoster virus characteristically produces vesicular pruritic disseminated Lesions at varying degrees of maturity. It occurs most frequently in children, with prodromal malaise, pharyngitis and rhinitis, usually with fever and pruritus (chickenpox). Varicella Zoster virus may cause more severe illness in adults, where the Lesions are Localized and painful, and often involve the trunk (shingles). Additional manifestations of HSY viral infection may include encephalitis and keratitis.

Although proposals have been made for a cure for the above diseases, an unmet need continues to exist for methods of preventing or treating a viral infection of a host.

SUMMARY

In the instant invention, depletion of human Pumilio 1 (PUM1) results in a cascade of events that Lead to the expression interferon (IFN) and interferon stimulated genes. In consequence infection of these cells with herpes simplex virus 1 (HSV-1) results in down regulation of viral gene expression and significant reduction of viral yields.

In this invention, we show that the consequences of depletion of PUM1 by transfection of uninfected cells with siRNA are diphasic. The first phase which extrapolates roughly to an interval between 12 and 24 hrs after transfection of siPUM1 RNA is characterized by a significant increase in the accumulation of transcripts encoding LGP2, CXCL10, IL6, and PKR. The second phase which extrapolates roughly to an interval between 24 and 48 hrs after transfection is characterized by an upsurge in the accumulation of mRNAs encoding RIG-I, MADS, SP100 PML and STING, IFNB and to a lesser extent that of IFNy. As could be expected from the array of upregulated expression of the selected genes associated with innate cellular immunity, infection of cells 24 h after transfection with siRNA resulted in significant decrease in viral gene products and viral yields.

In one aspect of the invention, a method for prophylaxis or treatment of infection of a virus in a subject is provided. The method comprises administering to the subject in need thereof a therapeutically effective amount of a PUM1 inhibitor.

In another aspect of the invention, a method for modulating innate immunity in a subject is provided. The method comprises administering to the subject in need thereof a therapeutically effective amount of a PUM1 inhibitor.

In a further aspect of the invention, a pharmaceutical composition for prophylaxis or treatment of infection of a virus, or for modulating innate immunity, in a subject, is proposed. The pharmaceutical composition comprises a therapeutically effective amount of a PUM1 inhibitor and a pharmaceutically acceptable carrier.

In a further aspect of the invention, provided is use of a PUM1 inhibitor in the preparation of a pharmaceutical composition for prophylaxis or treatment of infection of a virus in a subject or for modulating innate immunity in a subject.

In some embodiments of the invention, the virus is an interferon sensitive virus, in particular an interferon B sensitive virus. In certain embodiments, the virus is Herpes Simplex Virus type 1 or 2 (HSV-1 or HSV-2).

In some embodiments of the invention, the PUM1 inhibitor is a PUM1 selective inhibitor, i.e., an inhibitor specific to PUM1. In some embodiments, the PUM1 inhibitor is a generic inhibitor to members of PUM family, including PUM1, PUM2 and other members.

In some embodiments, the PUM1 inhibitor is selected from a compound intercalating between PUM1 and LGP2 and disrupting the interaction therebetween, a compound binding to PUM1 and blocking said interaction, a compound binding to LGP2 and blocking said interaction but not disrupting the function of LGP2, and an antisense oligomer delivered by a vesicle (e.g. an exosome) that targets to a nucleic acid molecule encoding PUM1 to block the synthesis of PUM1. In some embodiments, the nucleic acid molecule encoding PUM1 is selected from DNA encoding PUM1, RNA transcribed from the DNA, and cDNA derived from such RNA. In some embodiments, the antisense oligomer is selected from a DNA oligonucleotide, an RNA oligonucleotide (e.g., micro RNAs), and a chimeric oligonucleotide. For example, the antisense oligomer is selected from dsRNA, siRNA, and shRNA.

In some embodiment, the administration of the PUM1 inhibitor induces upregulated expressions of interferon and interferon stimulated genes. In some embodiment, the interferon stimulated genes is selected from LGP2, CXCL10, IL6, PKR, RIG-I, MAD5, SP100, IFIT1, PML and STING.

In some embodiment, the administration is carried out at least 12 to 72 hours before contact or potential contact of the virus. In some embodiment, the administration is carried out at least 48 to 72 hours before contact or potential contact of the virus. In preferable embodiments, the administration is carried out at least 72 hours before contact or potential contact of the virus.

The present invention demonstrated that depletion of PUM1 by siRNA resulted in production of interferon and activation of interferon stimulated genes. The response to depletion of PUM1 is diphasic. The phase 1 initiated between 12 and 24 h after transfection of siRNA results in expression of several gene known to regulate innate immune responses. Phase two, initiated sometime between 24 and 48 hrs results in accumulation of mRNAs encoding interferon and interferon stimulated genes. In the present invention, the impact of stimulated innate immune responses was demonstrated by diminished replication of herpes simplex virus 1 in cells exposed to spent medium from cell transfected with siRNA directed against PUM1. Pre-incubation of the spent medium with antibody against interferon diminished the inhibitory effects of the spent medium. The results suggest that reduction in the function of PUM1 may be a suitable approach to augmenting systemic host defenses against infectious agents.

The cells were harvested at 66 h after transfection. Cell lysates containing 70 µg of total proteins were separated on denaturing 10% polyacrylamide gels, electrically transferred to nitrocellulose sheets, and immunoblotted for PUM1 protein. 8-actin was used as a loading control. Panel B. Accumulation of selected cellular proteins in HEp-2 cells depleted of PUM1. 3×105 HEp-2 cells of seeded on 6-well plates were either mock treated or transfected with 100 nmol PUM1 siRNA or non-target siRNA (siNT). The cells were harvested at 36, 48 or 66 h after transfection. Lysates containing 70 µg of total proteins were separated on denaturing 100/o polyacrylamide gels, electrically transferred to nitrocellulose sheets, and immunoblotted for PUM1, IFIT1, PKR, PKR-P-Thr446, and STING. GAPDH was used as loading control. The images were scanned with the aid of ImageJ, and the density of the bands was normalized with respect to the loading controls and the values obtained for mock-transfected cells. siPUM1-1777: 5' GCUGCUUAC-UAUGACCAAATT 3' (SEQ ID NO: 1); siPUM1-2652: 5' GGAGAUUGCUGGACAUAUATT 3' (SEQ ID NO: 2); siNT: 5' UUCUCCGAACGUGUCACGUTT 3' (SEQ ID NO: 3).

Figure 2:
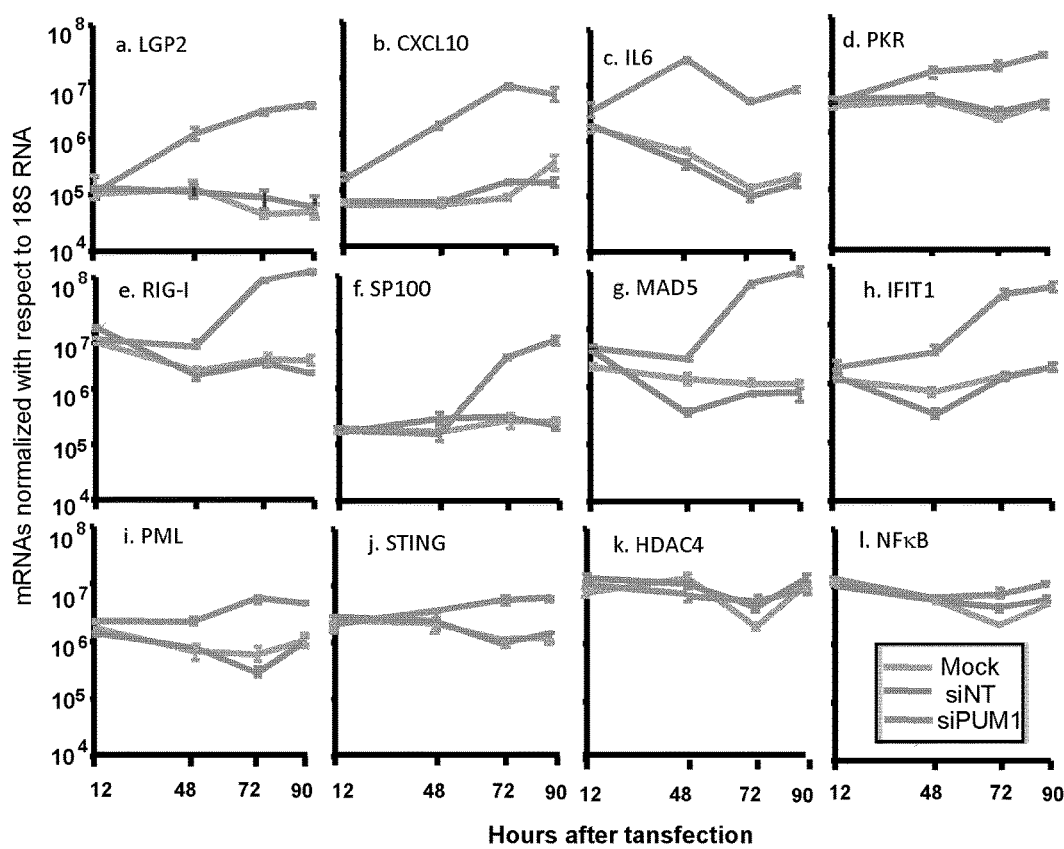

FIG. 2. Accumulation of mRNAs of selected cellular genes in HEp-2 cells at times after mock transfection or transfection of NT and PUM1 siRNAs HEp-2 cells seeded on 6-well plates were either mock treated or transfected with 100 nmol of PUM1 siRNA or non-target siRNA (siNT). The cells were harvested at 12 h, 48 h, 72 h or 90 h after transfection. Total RNAs were extracted and reverse transcribed to cDNA as described in Materials and Methods. mRNA levels LGP2, CXCL10, IL6, PKR, RIG-I, SP100, MDA-5, IFIT1, PML, STING, HDAC4, and NFκB were norn RNA.

Figure 1:
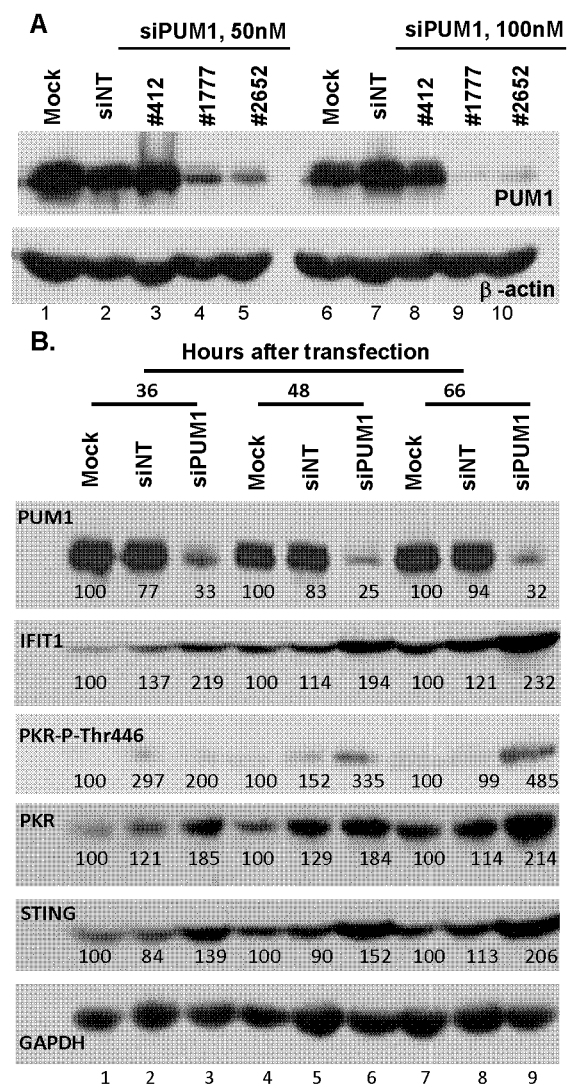
FIG. 1. Depletion of PUM1 in HEp-2 cells resulted in upregulation of selected cellular proteins. Panel A. Depletion of PUM1 by transfection of siRNA. 3×105 HEp-2 cells seeded on 6-well plates were either mock treated or transfected with 50 or 100 nmol PUM1 siRNA or non-target siRNA (siNT).
Figure 3:
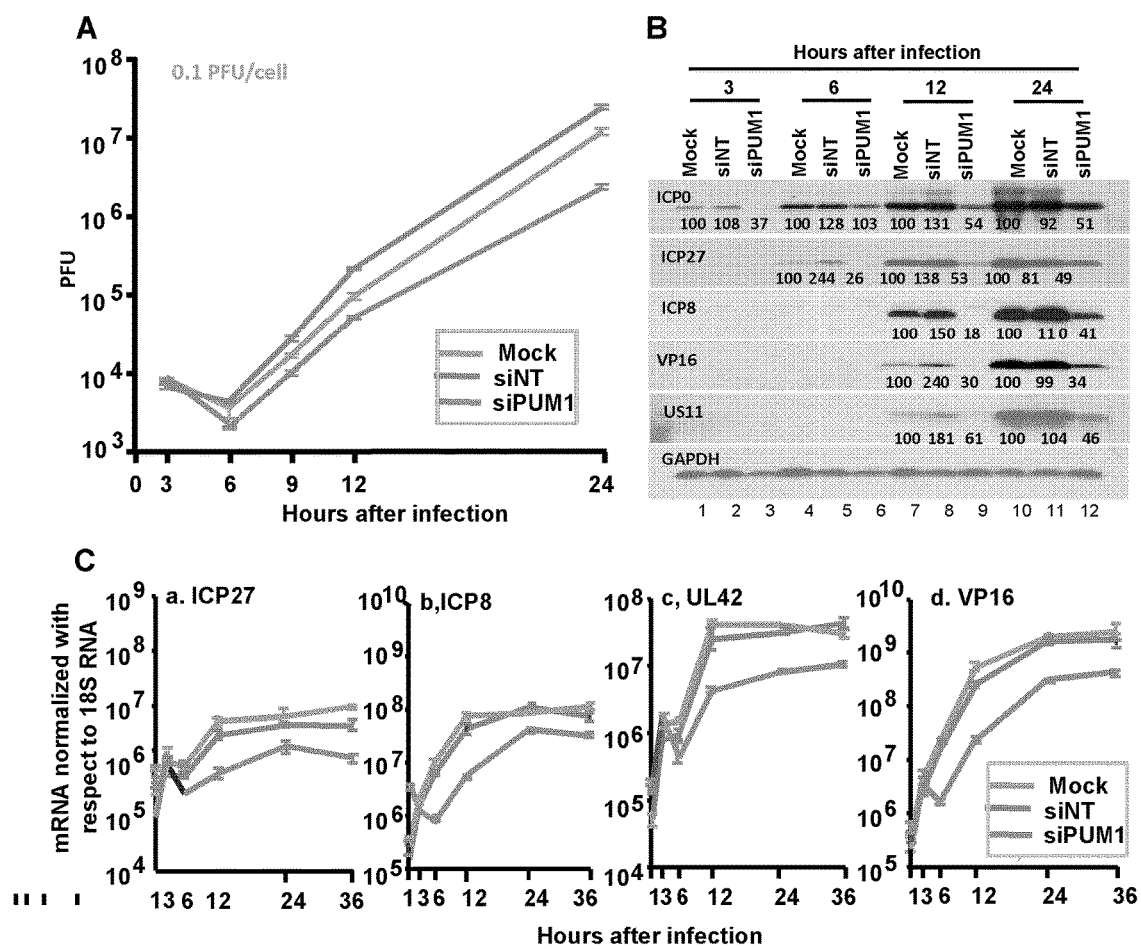

FIG. 3. Accumulation of infectious virus, representative viral proteins or viral mRNAs in cells mock transfected or transfected with NT or PUM1 siRNA. Panel A. Virus yields in PUM1-depleted cells. Replicate cultures of HEp-2 cells in 6-well were either mock treated or transfected with 100 nmol PUM1 siRNA or irrelevant non-target siRNA (siNT). After 48 h of incubation, the cells were exposed to 0.1 PFU of HSV-1 (F) per cell for 1 h. The inoculum then was replaced with fresh medium. The virus progeny were harvested at the times shown and were titered in Vero cells. Panel B. Accumulation of selected viral proteins in PUM1-depleted cells. HEp-2 cells in 6-well plates were either mock treated or transfected with 100 nmol PUM1 siRNA or non-target siRNA (siNT) for 66 h. The cells were then exposed to 0.5 PFU of HSV-1 (F) per cell and harvested at 3, 6, 12 or 24 h after infection. The proteins were electrophoretically separated in a 10% denaturing gel and reacted with indicated antibodies. The protein bands were scanned and quantified as described in the legend to FIG. 1. Panel C. Accumulation of selected viral mRNAs in PUM1-depleted cells. HEp-2 cells were mock-transfected, or transfected with NT siRNA or PUM1 siRNA with PUM1 siRNA and then infected with 0.5 PFU of HSV-1 (F) per cell as described in Panel B. The cells were harvested at 1, 3, 6, 12, 24 or 36 h after infection. Total RNAs were extracted, reverse transcribed to cDNA as described in Materials and Methods. The mRNAs of viral ICP27, ICP8, UL42 or VP16 were quantified and normalized with respect to 185 RNA.

Figure 4:
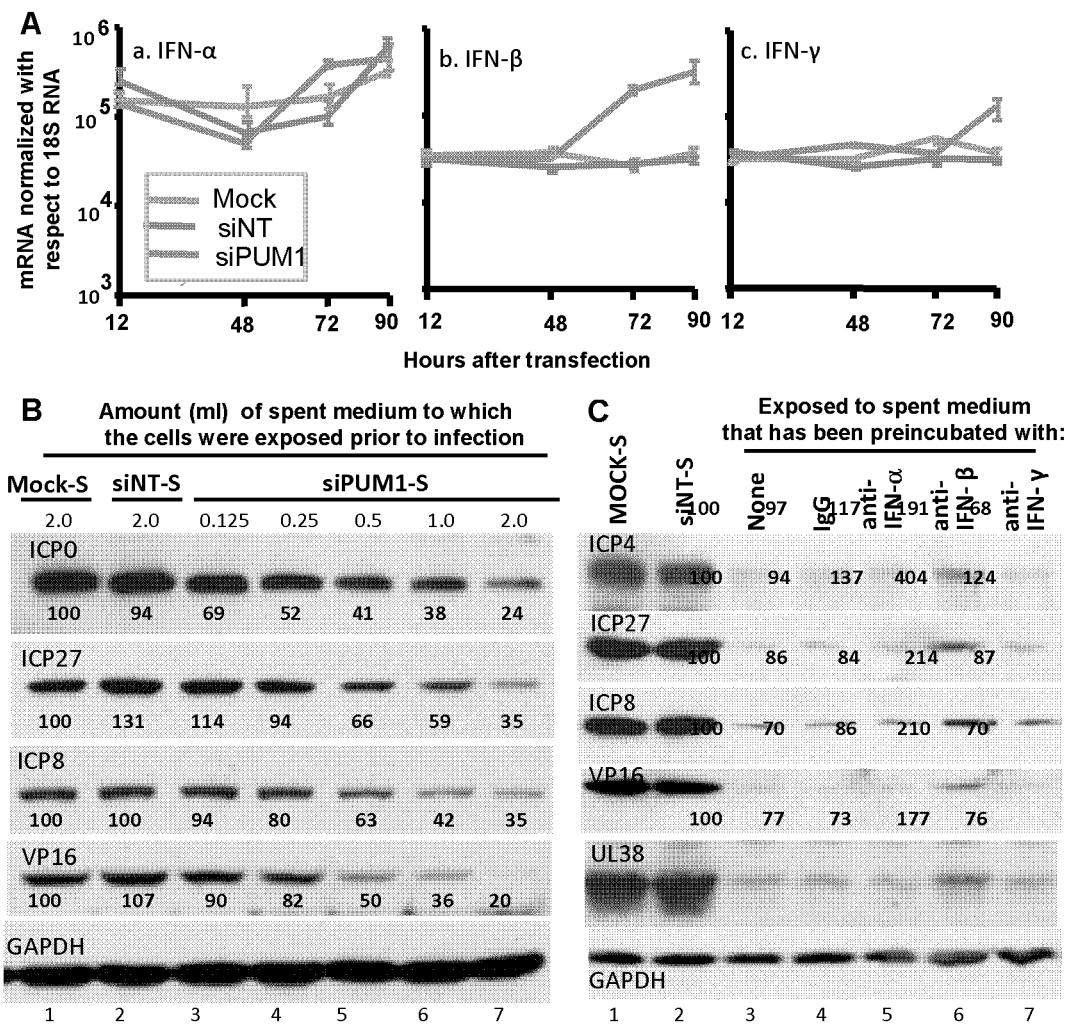

FIG. 4. Depletion of PUM1 resulted in the accumulation of IFN-8 mRNA and diminished accumulation of selected HSV-1 proteins. Panel A. Depletion of PUM1 resulted in the accumulation of IFN-8 mRNA. 3×105 HEp-2 cells seeded in 6-well plates were either mock treated or transfected with 100 nmol PUM1 siRNA or non-target siRNA (siNT). The cells were harvested at 12 h, 48 h, 72 h or 90 h after transfection. Total RNAs were extracted, reverse transcribed to cDNA as described in Materials and Methods. mRNA expression of IFN-α, IFN-β and IFN-γ were normalized with respect to 185 RNA. Panel B. Spent medium harvested from cultures of PUM1-depleted cells blocked HSV-1 replication in a dose-dependent manner Spent medium collected from HEp-2 cells either with mock treated or transfected with 100 nmol PUM1 siRNA or non-target siRNA (siNT) for 48 h. Fresh HEp-2 cells were incubated with the spent medium with indicated amount for 24 h then infected with 0.1 PFU of HSV-1(F) per cell. The cell lysates were collected 24 h post-infection, denatured, electrophoretically separated in a 10% denaturing gel and reacted with indicated antibodies. Panel C. Anti-IFNβ but not anti INFα or anti INFγ attenuated the anti-viral effects of spent medium collected from cultures of PUM1 depleted cells. 2 ml amounts of spent medium collected from mock treated, transfected with NT siRNA or with PUM1 siRNA were incubated with antibodies against lgG (25 μg), IFNa (12.5 μg), IFNB (25 μg) or IFNy (25 μg) at 37° C. for 2 h. Fresh HEp-2 cells in 12-well plate were incubated with the spent medium pre-incubated with IFN antibodies described above for 24 h then infected with 0.1 PFU of HSV-1(F) per cell. The cell lysates were collected at 24 h post-infection and electrophoretically separated in a 10% denaturing gel and reacted with indicated antibodies.

Figure 5:
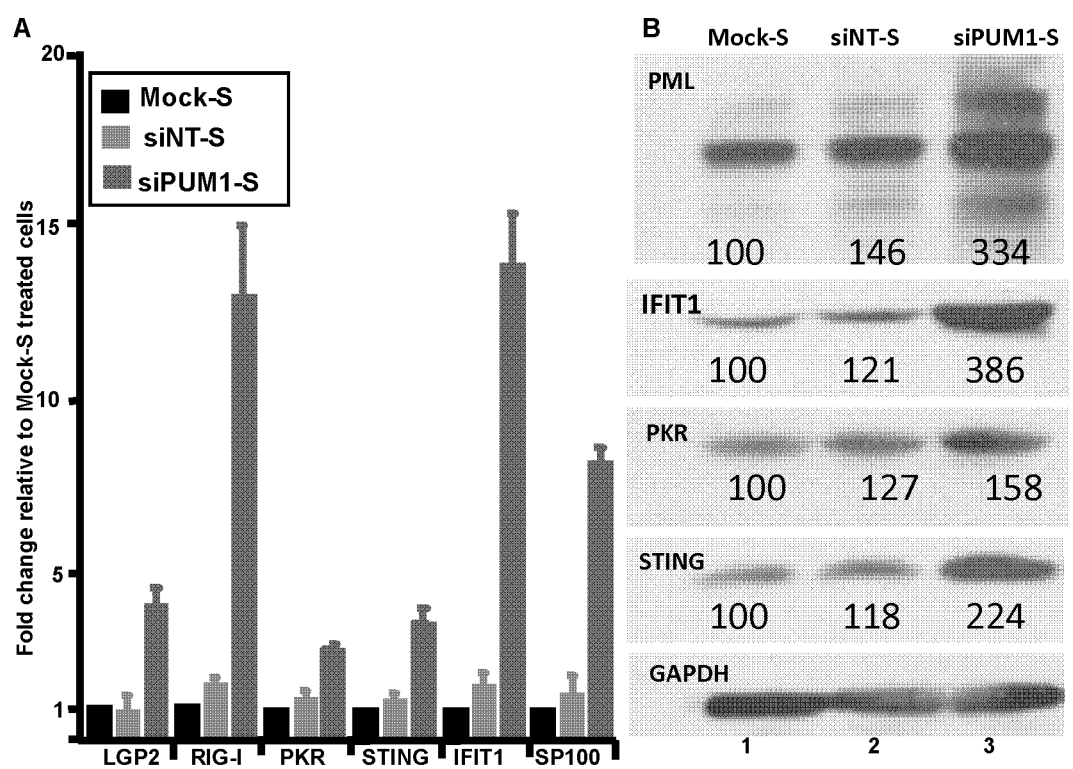

FIG. 5. Depletion of PUM1 resulted in accumulation of IFN-stimulated gene (ISGs) products. Panel A. mRNA accumulation of ISG mRNAs in cells exposed to spent medium collected from mock treated, transfected with NT or PUM1 siRNAs. HEp-2 cell cultures were mock transfected or transfected with 100 nmol PUM1 siRNA or non-target siRNA (siNT) After 48 h the spent medium was collected and overlayed on fresh cultures of HEP-2 cells. After 20 h the cells were processed as described in Panel A of FIG. 4. The figure in Panel A shows the amounts of mRNAs for several ISGs normalized with respect to 18s RNA. Panel B. Accumulation of ISG proteins in PUM1-depleted cells. The experimental design is identical to that shown in FIG. 5A. The lysates of cell were collected 24 h after exposure to spent media were electrophoretically separated in a 10% denaturing gel and reacted with indicated antibodies.

DETAILED DESCRIPTION

Definitions

It is to be noted that the term "a" or "an" entity refers to one or more of that entity; for example, "a recombinant oncolytic HSV-1," is understood to represent one or more recombinant oncolytic HSV-1 viruses. As such, the terms "a" (or "an"), "one or more," and "at least one" can be used interchangeably herein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not Limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on. The subject herein is preferably a human.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

The present invention employs, among others, antisense oligomer and similar species for use in modulating the function or effect of nucleic acid molecules encoding Pumilio 1, also referred to as PUM1. This is accomplished by providing oligonucleotides which specifically hybridize with one or more nucleic acid molecules encoding Pumilio 1. As used herein, the terms "target nucleic acid" and "nucleic acid molecule encoding Pumilio 1" have been used for convenience to encompass DNA encoding Pumilio 1, RNA (including pre-mRNA and mRNA or portions thereof) transcribed from such DNA, and also cDNA derived from such RNA. The hybridization of an oligomer of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at Least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of Pumilio 1. In the context of the present invention, "modulation" and "modulation of expression" mean decrease (inhibition) in the amount or levels of a nucleic acid molecule encoding the gene, e.g., DNA or RNA. mRNA is often a preferred target nucleic acid.

In the context of this invention, "hybridization" means the pairing of complementary strands of oligomers. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense oligomer is specifically hybridizable when binding of the oligomer to the target nucleic acid interferes with the normal function of the target nucleic acid to cause a loss of activity, and there is a sufficient degree of complementarity to avoid non-specific binding of the antisense oligomer to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomers and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense oligomer need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense oligomer are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense oligomer which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art.

Furthermore, nucleotide or amino acid substitutions, deletions, or insertions leading to conservative substitutions or changes at "non-essential" amino acid regions may be made. For example, a polypeptide or amino acid sequence derived from a designated protein maybe identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

Exemplary preferred antisense oligomers include oligonucleotide sequences those described in US Patent Publication 20050261217 A1. The entire disclosure of the application is incorporated herein by reference. One having skill in the art armed with the preferred antisense oligomers illustrated herein will be able, without undue experimentation, to identify further preferred antisense oligomers.

In the context of this invention, the term "interferon sensitive virus" or "interferon 8 sensitive virus" is a virus with its replication capability capable of being reduced, impaired, inhibited or eliminated, partially or wholly, by co11tatct11ng with an interferon or in particular interferon 8. The presence of and/or production of interferon has a beneficial effect in terms of inhibition, dormancy, elimination or clearance of the virus from the subject.

PUM1 Inhibitor

The PUM1 inhibitor of the present invention is an agent capable of inhibiting or reducing the level of the PUM1 protein in a cell. A PUM1 inhibitor prevents PUM1 from blocking activation of innate immune responses. PUM1 may have functions that are not directly related to blocking innate immune responses (e.g. binding of mRNA). PUM1 suppresses activation of innate immunity by binding to LGP2 and blocking activation of innate immune responses that include the production of interferon.

Therefore, a PUM1 inhibitor maybe a chemical molecule that intercalates between PUM1 and LGP2 and disrupts the interaction; a chemical molecule that binds to PUM1 and blocks the interaction, a chemical molecule that binds to LGP2 and blocks the interaction but does not disrupt the function of LGP2, or a micro RNA delivered by vesicles (e.g. exosomes) that blocks the synthesis of PUM1.

Since PUM functions inside the cell, an antibody to PUM1 or LGP2, direct administration of antisense RNA, or any molecule that cannot penetrate into uninfected cells by itself, are not within the meaning of a PUM1 inhibitor as defined herein.

On exposure to a virus, the infected cells attempt to respond by inducing a response to block virus replication and spread. At best it is a local response not effective even a short distance away. Thus notwithstanding a "local" response to infection the virus can replicate and spread to "distant" sites. Here the word distant means a cell not in immediate contact to the infected cell. One use of a PUM1 inhibitor is to induce a "universal, full body response" to infection so that viruses transported to a distant site from initial infection are arrested and cannot replicate. One example of the use of a PUM1 inhibitor is to use it within a short time after the onset of a respiratory infection.

In one embodiment, the level of PUM1 protein is represented by the amount of protein existing in a cell. Alternatively, the level of PUM1 protein is represented by the mRNA level in a cell. In some embodiments, the level of PUM1 protein can be inhibited or reduced by inhibiting any of the transcription or translation procedures involved in the expression of PUM1 protein in a cell. In some embodiments, a siRNA directed to a fragment of the nucleic acid encoding PUM1 protein is used, as given in the examples. Other RNAi technologies are well known in the art to inhibit, reduce, or deplete the expression of the PUM1 in a cell. Enzymes or components involved in the expression of the PUM1 protein from its encoding nucleic acid can also be targeted to inhibit and reduce the production of PUM1 protein, such as RNAse H.

Virus and Virus Infection

As used herein, the virus, or interferon sensitive virus can be an orthomyxovirus (e.g., influenza virus), Adenovirus, arbovirus, paramyxovirus, baculovirus, coronavirus, papillomavirus, parvovirus, chickenpox virus, reovirus, Ebola virus, Ebola-like virus, echo virus, encephalitis virus, filovirus, hantavirus, hepatitis virus, German measles virus, cytomegalovirus, hemorrhagic fever virus, herpes simplex virus 1, herpes simplex virus 2, hepatitis A virus, hepatitis B virus, hepatitis C virus, human immunodeficiency virus (HIV), human papillomavirus (the causative agent of genital warts), human T cell leukemia virus, human T cell lymphoma virus, human T cell lymphotropic virus, Lassa fever virus, Marburg virus, measles virus, mumps virus, myxovirus, nairovirus, nanirnavirus, nariva virus, ndumo virus, Necrovirus, neethling virus, neopvirus, neurotropic virus, Newcastle disease virus, oncornavirus, orbivirus, parainfluenza virus, paramyxovirus, parvovirus, picornavirus, rabies virus, respiratory syncytial virus, rhinovirus, rubella virus, rubeola virus, SARS virus, Sendai virus, simian immunodeficiency virus, simian parainfluenza virus, smallpox virus, varicella zoster virus, variola virus, or a vesicular stomatitis virus (VSV).

As used herein, the term "infection" means the invasion by, multiplication and/or presence of a pathogen in a cell, tissue, or subject. In one embodiment, an infection is an "active" infection, i.e., one in which the pathogen is replicating in a cell, tissue, or subject. Such an infection may be characterized by the spread of the pathogen to other cells, tissues, organs, and/or subjects from the cells, tissues, organs, and/or subjects initially infected by the pathogen. An infection may also be a latent infection, i.e., one in which the pathogen is not replicating. In one embodiment, an infection refers to the pathological state resulting from the presence of the pathogen in a cell, tissue, or subject, or by the invasion of a cell, tissue, or subject by the pathogen.

Methods and Therapies

An aspect of the disclosure provides a method for prophylaxis or treatment of infection of a virus in a subject comprising administering to the subject in need thereof a therapeutically effective amount of a PUM1 inhibitor or a pharmaceutical composition comprising a PUM1 inhibitor. Equally, the disclosure provides the PUM1 inhibitor as described above for use in a method for treating or alleviating symptoms involved with virus infection.

In certain embodiments, the PUM1 inhibitor or the pharmaceutical composition is administered parenterally, e.g. intravenously, intramuscularly, percutaneously or intracutaneously.

In some embodiments, it may be desirable to combine a PUM1 inhibitor with other agents effective in the treatment of virus infection. For example, the treatment of a virus infection may be implemented with a PUM1 inhibitor and other anti-virus therapies, such as anti-virus agents.

The therapy may precede or follow the other agent treatment by intervals ranging from minutes to weeks. In embodiments where the other agent and PUM1 inhibitor are applied separately to the subject, one would generally ensure that a significant period of time did not expire between the time of each delivery, such that the agent and PUM1 inhibitor would still be able to exert an advantageously combined effect on the subject. In such instances, it is contemplated that one may administer the subject with both modalities within about 12 to 72 hrs of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In the context of prophylaxis or treatment of infection of a virus in a subject, the method is performed at least 12 to 72 hrs before contact or potential contact with the virus. In some embodiments, the method is performed at least 24 to 72 hrs prior to the contact or potential contact with the virus. In preferable embodiment, the method is performed at least 72 hrs prior to the contact or potential contact.

In certain embodiments, the methods of treating a viral infection prevent the progression of the infection and/or the onset of disease caused by the viral infection. Thus, in some embodiments, a method for preventing the progression of a viral infection and/or the onset of disease caused by the viral infection, comprises administering an effective amount of a PUM1 inhibitor to a subject in need thereof. In certain embodiments, the methods of treating a viral infection prevent the onset, progression and/or recurrence of a symptom associated with a viral infection. Thus, in some embodiments, a method for preventing a symptom associated with a viral infection in a subject, comprises administering an effective amount of a PUM1 inhibitor to a subject in need thereof.

Another aspect of the disclosure provides a method for modulating innate immunity in a subject comprising administering to the subject in need thereof a therapeutically effective amount of a PUM1 inhibitor or a pharmaceutical composition comprising a PUM1 inhibitor.

The PUM1 inhibitor of the invention have been shown to have therapeutic utility in enhancing innate immunity. The enhancement of innate immunity is demonstrated by upregulation, in mammalian cells, of genes that are natural components of the innate immune response, including LGP2, CXCL10, IL6, PKR, RIG-I, MAD5, SP100, IFIT1, PML and STING.

The PUM1 inhibitor of the invention can be used to modulate innate cellular immunity in a subject and/or for the treatment of an immune-related disorder, including treating and preventing infection by modulating immunity.

Compositions

An aspect of the present invention provides a pharmaceutical composition comprising a therapeutically effective amount of a PUM1 inhibitor and a pharmaceutically acceptable carrier. The pharmaceutical composition is useful for prophylaxis or treatment of infection of a virus, or for modulating innate immunity, in a subject. The PUM1 inhibitor may be prepared in a suitable pharmaceutically acceptable carrier or excipient. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologies standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

EXAMPLES

Materials and Methods

Cells and Viruses.

HSV-1 (F) is a limited-passage prototype strain used in this laboratory (Ejercito et al., 1968). HEp-2 and HEK293T cells were obtained from the American Type Culture Collection (Rockville, Md.). All cells were grown in Dulbecco's modified Eagle's medium containing 10% fetal bovine serum.

Depletion of PUM1 Protein Level in HEp-2 Cells by siRNA.

All transfections were carried out using Lipofectamine 2000 (Invitrogen) by its manufacturer's instructions. The target sequence of the PUM-1 siRNA was 5' GCUGCUUA-CUAUGACCAAATT 3' (SEQ ID NO: 1) (siPUM1-1777). The non-targeting (NT) siRNA (GenePharma) was used as negative control (siNT: 5' UUCUCCGAACGUGU-CACGUTT 3') (SEQ ID NO: 3).

RNA Extraction and Measurements by Real-Time Quantitative PCR.

Total RNAs were extracted with the aid of TRI Reagent solution (Thermo Scientific) according to the manufacturer's instructions, standardized by optical density measurements, and then treated with DNase I (Takara). Viral and cellular cDNA were synthesized from 0.5 µgot' total RNA with the aid of the ReverTra Ace® q-PCR RT Kit (Toyobo) using primers listed in Table 1 in accordance with instructions provided by the suppliers. Viral and cellular DNA copy numbers were then quantified by SYBR green real-time PCR technology (Toyobo), normalized with respect to 18S RNA.

Immunoblot Assays.

Cells were collected at the indicated times after infection. The procedures for harvesting, solubilization, protein quantification, SDS/PAGE, and transfer to nitrocellulose membranes were as described previously (Zhou et al., 2010). Images were quantified with Image J by integration pixel values across the area of specific bands.

Antibodies.

Antibodies against to HSV-1 ICP4 (Ackermann et al., 1984), ICP27 (Ackermann et al., 1984), ICP8 (Rumbaugh Goodwin Institute for Cancer Research, Inc.), VP16 (Mcknight et al., 1987), UL38 (Ward et al., 1996), and US11 (Roller and Roizman, 1992) have been reported elsewhere. The antibody against GAPDH was purchased from Cell Signaling Technology. These studies used rabbit monoclonal antibodies against PUM1 (Abcom, 92545), PKR (Abcom, 32506), PKR-pT446 (Abcom, 32036), PML (Abeam, 179466), IFIT1 (CST, D2X9Z), GAPDH (CST, 2118), 8-actin (Proteintech, 60008-1-1g) and rabbit polyclonal against STING (Proteintech, 19851-1-AP).

Virus Titration.

HEp-2 cells were transfected with 100 nM of PUM1 siRNA. After 48 h the cells were exposed to 0.1 PFU of HSV-1 (F) per cell. The cells were harvested at indicated times after infection. Viral progeny was titrated on Vero cells.

Assays of Spent Medium.

Spent medium collected 48 h after transfection of HEp-2 cells with 100 nM of PUM1 siRNA was overlayed on fresh cultures of HEp-2 cells as described in Results. The treated cell cultures were harvested for quantitative PCR assay of indicated host cell mRNAs or exposed to 0.1 PFU/cell HSV-1 (F) and harvested at 24 h after infection for viral proteins expression assay.

IFN Neutralization Assay.

2 ml amounts of spent culture medium harvested from HEp-2 cells transfected with 100 nM of PUM1 siRNA for 48 h were incubated with either anti-IgG (Proteintech, B900610), anti-IFNα (PBL, 21118-1), anti-IFNβ (R&D Systems, MAB814-100), or anti-IFNγ (R&D Systems, MAB285-100) antibodies at 37° C. for 2 h. Fresh HEp-2 cells grown in 12-well plates were then exposed to the mixtures of spent medium and antibodies as described above. After 24 h of incubation the cultures were exposed to 0.1 PFU/cell HSV-1 (F) and harvested at 24 h after infection.

TABLE 1

Sequences of primers used to measure gene expression.

| Gene | Forward primer | Reverse primer |
| --- | --- | --- |
| LGP2 | 5'-GAGCCAGTACCTAGAACTTAAAC-3' (SEQ ID NO: 4) | 5'-ATGGCCCCATCGAGTTTG-3' (SEQ ID NO: 5) |
| CXCL10 | 5'-ACGTGTTGAGATCATTGCTAC-3' (SEQ ID NO: 6) | 5'-ATCTTTTAGACCTTTCCTTGC-3' (SEQ ID NO: 7) |
| IL6 | 5'-GCCACTCACCTCTTCAGAACG-3' (SEQ ID NO: 8) | 5'-CAGTGCCTCTTTGCTGCTTTC-3' (SEQ ID NO: 9) |
| PKR | 5'-GGAAAGCGAACAAGGAGTAAG-3' (SEQ ID NO: 10) | 5'-ATCCCGTAGGTCTGTGAAAAAC-3' (SEQ ID NO: 11) |
| RIG-I | 5'-AGAAGAGTACCACTTAAACCCAG-3' (SEQ ID NO: 12) | 5'-TTGCCACGTCCAGTCAATATG-3' (SEQ ID NO: 13) |
| SP100 | 5'-TTTTCGCCTCAGAACCGTATT-3' (SEQ ID NO: 14) | 5'-CTGCACAAACCCTTCTACTCG-3' (SEQ ID NO: 15) |
| MDA-5 | 5'-AGGAGTCAAAGCCCACCATC-3' (SEQ ID NO: 16) | 5'-GTGACGAGACCATAACGGATAAC-3' (SEQ ID NO: 17) |

TABLE 1-continued

Sequences of primers used to measure gene expression.

| Gene | Forward primer | Reverse primer |
| --- | --- | --- |
| IFIT1 | 5'-CAACCAAGCAAATGTGAG-3' (SEQ ID NO: 18) | 5'-AGGGGAAGCAAAGAAAATGG-3' (SEQ ID NO: 19) |
| PML | 5'-CACCCGCAAGACCAACAACATC-3' (SEQ ID NO: 20) | 5'-GCTTGGAACATCCTCGGCAGTAG-3' (SEQ ID NO: 21) |
| STING | 5'-TCAGCATTACAACAACCTGCTAC-3' (SEQ ID NO: 22) | 5'-TTATCCAGGAAGCGAATGTTG-3' (SEQ ID NO: 23) |
| HDAC4 | 5'-TCAAGAACAAGGAGAAGGGCAAAG-3' (SEQ ID NO: 24) | 5'-TCCCGTACCAGTAGCGAGGGTC-3' (SEQ ID NO: 25) |
| NFkB1 | 5'-TAAAGCCCCCAATGCATCCAAC-3' (SEQ ID NO: 26) | 5'-CCAAATCCTTCCCAGACTCCAC-3' (SEQ ID NO: 27) |
| IFN-α | 5'-AGAGTCACCCATCTCAGCAAG-3' (SEQ ID NO: 28) | 5'-CACCAGGACCATCAGTAAAGC-3' (SEQ ID NO: 29) |
| IFN-β | 5'-TTGTGCTTCTCCACTACAGC-3' (SEQ ID NO: 30) | 5'-CTGTAAGTCTGTTAATGAAG-3' (SEQ ID NO: 31) |
| IFN-γ | 5'-ATGTCCAACGCAAAGCAATAC-3' (SEQ ID NO: 32) | 5'-GCTCTTCGACCTCGAAACAG-3' (SEQ ID NO: 33) |
| ICP27 | 5'-TCATGCACGACCCCTTTGG-3' (SEQ ID NO: 34) | 5'-CTTGGCCCGCCAACAC-3' (SEQ ID NO: 35) |
| ICP8 | 5'-GCCTGAAACACACGGTCGTT-3' (SEQ ID NO: 36) | 5'-ATGGTCGTGTTGGGGTTGAG-3' (SEQ ID NO: 37) |
| UL42 | 5-TTTCTCCTGAAACCCCAGAAGATTTG-3' (SEQ ID NO: 38) | 5'-AGTCCTGGCTGTCTGTTGGCTC-3' (SEQ ID NO: 39) |
| VP16 | 5'-CTCGAAGTCGGCCATATCCA-3' (SEQ ID NO: 40) | 5'-CCGGGTCCGGGATTTACC-3' (SEQ ID NO: 41) |
| 18S | 5'-CTCAACACGGGAAACCTCAC-3' (SEQ ID NO: 42) | 5'-CGCTCCACCAACTAAGAACG-3' (SEQ ID NO: 43) |

Results

PUM1 Mediates the Suppression of Selected Genes Known to Play a Significant Role in Innate Immune Responses to Infection In this series of experiments we measured the accumulation of protein and mRNAs of selected cellular genes associated with innate immune responses in cells depleted of PUM1 after transfection of targeted (siPUM1) or non-targeted (siNT) siRNAs. The sequence of siRNAs employed in these studies, the sequences of the probes for quantification of mRNAs and the sources of antibodies are described in Materials and Methods.

In preliminary studies we have identified a NT siRNA and two siRNAs (#1777 and #2652) suitable for these studies. The results shown in FIG. 1A indicate that siPUM1 #1777 at 100 nM is suitable for depletion of PUM1 whereas siNT had no negative effect on accumulation of PUM1.

We next examined the effect of depletion of PUM1 on the accumulation of IFIT1, PKR, PKR-p-Thr446 and STING. The quantity of protein shown below the bands were normalized with respect to mock transfected level and GAPDH levels measured in the assays. The results (FIG. 1B lanes 7-9) show that at 66 hrs after transfection the amounts of the proteins analyzed in this study increased at least two fold. The amounts of PKR-p-Thr446 increased 4.8 fold. Smaller increases were noted at 48 hrs after transfection.

We next examined the accumulation of mRNAs of a selected set of 12 cellular genes. In this instance the amounts of mRNAs were normalized with respect to 18S RNAs. The results are shown in FIG. 2. In brief few changes in mRNA levels were noted at 12 h after transfection of siRNAs. At later times after transfection we noted 3 different responses. Specifically the mRNA levels of LGP2, CXCL10, IL6, and PKR began to increase sometime between 12 and 48 h after transfection and leveled off between 72 to 96 h after transfection. The levels of RIG-I, SP100 MADS IFIT1 and to a lesser extent those of PML and STING increased after 48 hrs after transfection. Lastly, we did not detect a significant increase in the levels of mRNAs encoding HDAC4, and NFκB within the time interval tested.

In summary the results show that the expression of at least 10 genes associated with innate immune responses are upregulated in uninfected HEp-2 cells depleted of PUM1. The increases in expression of some genes extrapolate to approximately 12 h after transfection. In the case of others, notably RIG-I, SP100, IFIT1, MADS, PML and STING the increases in the accumulation of mRNAs began between 48 and 72 h after transfection. One hypothesis that could explain the results is that the genes whose increase in expression began after 48 h after transfection were activated by the products of genes transactivated between 12 and 48 h after transfection.

Depletion of PUM1 has a Negative Effect on the Replication of HSV-1

The objective of this series of experiments was to determine the effect of PUM1 depletion on the replication of HSV-1. Replicate HEp-2 cell cultures were exposed to 0.1 PFU of HSV-1 (F) per cell 24 hrs after transfection with siNT or siPUM1 mRNA. The results (FIG. 3) indicate that the replication of HSV-1 was impaired and resulted in reduced virus yields (FIG. 3A), reduced accumulation of proteins (FIG. 3B) associated with different kinetic classes (e.g. ICPO and 27 representative of the a or immediate early genes, ICP8 representative of the 8 genes and VP16 and US11 representative of y or late genes), and decreases in the accumulations of viral mRNAs (FIG. 3C). The decreases in the accumulation of viral gene products are consistent with the increases of expression of genes associated with innate immunity.

Cells Transfected with siPUM1 Make IFNβ

The activation of genes associated with innate immunity and reductions in viral yields and viral gene products raised the question whether depletion of PUM1 results in production of interferon. The results presented below suggest that this is the case.

Cells mock-treated or transfected with 100 nM of siNT or siPUM1 were harvested at 12, 48, 72, or 90 hrs after transfection and analyzed for the accumulation of mRNAs encoding IFNα, IFNβ or IFNγ using procedures and probes described in Materials and Methods. The results shown in FIG. 4A suggest that IFNβ RNA begins to accumulate between 48 and 72 h after infection. The assays also detected the accumulation of small amounts of IFNβ mRNAs.

Next we tested for anti-viral inhibitory activity of spent medium harvested 48 h after mock transfection or transfection with 100 nmol of siNT or siPUM1. In these experiments replicate cultures of HEp-2 cells in 6-well plates were exposed to amounts of spent medium ranging from 0.125 to 2 mls. After 24 h of incubation the cells were exposed 0.1 PFU of HSV-1 (F) per cell. The cells were harvested 24 h after infection and analyzed for the accumulation of viral proteins representative of differed kinetic classes. The results (FIG. 4B) show that the yields of viral proteins were not affected by the exposure to 2 ml of spent medium from cultures of mock-transfected or siNT transfected cells. Infected cells exposed to spent medium from culture transfected with siPUM1 yielded less viral proteins in a dose dependent fashion.

We next tested whether the inhibitor present in spent medium of cells transfected with siPUM1 was IFN. In these experiments 2 ml aliquots of the spent medium from siPUM1 transfected cells (siPUM1-5) were incubated for 2 h at 37° C. with antibody to IFNα, IFNβ or IFNγ as detailed in Materials and Methods. Replicate HEp-2 cell cultures were then exposed to 2 ml amounts of Mock-5, siNT-S, or siPUM1-S or the siPUM1-S—antibody mixtures. After 24 h after the cells were exposed to 0.1 PFU of HSV-1 (F). FIG. 4C shows the accounts of various viral proteins present cells harvested 24 h after infection. The results suggest that the spent medium harvested from cells transfected with siPUM1 contained INFO inasmuch as cells exposed to spent medium neutralized with anti IFNβ accumulated 2 to 4 fold more proteins than the controls. We did not detect evidence of antiviral effects due to IFNβ (FIG. 4C lane 7).

Additional data supporting the hypothesis that cell depleted of PUM1 secret interferon into extracellular fluid is based on two series of experiments. Thus cells exposed to Mock-S, siNT-S or siPUM1-S as above were harvested 20 hrs after transfection and analyzed with respect to the level of mRNAs encoding known ISGs. The procedures were the same as those employed in preceding experiments (FIG. 2). The results (FIG. 5A) show that the spent medium from cells incubated with siPUM1 significantly upregulated the mRNA encoding LGP2, RIG-I, STING, IFIT1 and SP100. Although the upregulation of PKR was significant, it was lower than that of other genes tested in this assay.

In the second experiment we examined the accumulation of several ISG proteins in lysates of cells maintained in Mock-S, siNT-S or siPUM1-S for 24 hrs. The procedures were as descried earlier in the text. The results (FIG. 5B) show that the cells exposed to siPUM1-S expressed levels of PML, IFIT1 and STING more than two-fold higher than those exposed to Mock-S. Again in this assay the upregulation of PKR was lower than that of other genes tested in this assay.

The present invention shows that disruption of PUM1 results in a significant upregulation of numerous genes whose products play a key role in innate immunity. These include RIG-I, PML, SP100, IFIT1, STING and ultimately IFNβ. The significance of this observation stems from the following considerations:

In the course of viral infection, cellular sensors detect the presence of foreign nucleic acids. The sensors activate the synthesis of interferons which in turn activate the expression of the "Interferon Stimulated Genes" (ISGs) both in the infected cells and following IFN secretion, in adjacent cells. Viruses have in turn evolved mechanisms that curtail or reduce the repressive effects of innate immune responses and block or reduce the synthesis or the impact of innate immune responses. The significance of the studies reported here stem from the observation that innate immune response and in particular ISGs activated before infection are far more effective in curtailing the growth of pathogens than the innate immune responses activated after infection.

The present invention teaches that PUM1 is a master regulator of innate immune responses resulting in production of interferon and reduction of in the replication of infectious agents. It could be visualized that at first signs of infection administration of medication that suppresses the functions of PUM1 would result in enhancement of innate immunity, suppression of virus spread and rapid shutoff of viral infections.

It should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The invention claimed is:

1. A method for treatment of infection of a virus in a subject, comprising administering to the subject a therapeutically effective amount of a PUM1 inhibitor, wherein the PUM1 inhibitor is an antisense oligomer that targets a nucleic acid molecule encoding PUM1 to block the synthesis of PUM1 wherein the virus is Hepres Simplex Virus type 1 or type 2.

2. The method of claim 1, wherein the virus is an interferon sensitive virus.

3. The method of claim 1, wherein the antisense oligomer is delivered by a vesicle.

4. The method of claim 1, wherein the nucleic acid molecule encoding PUM1 is selected from DNA encoding PUM1, RNA transcribed from the DNA, and cDNA derived from such RNA.

5. The method of claim 1, wherein the antisense oligomer is selected from a DNA oligonucleotide, an RNA oligonucleotide, and a chimeric oligonucleotide.

6. The method of claim 5, wherein the antisense oligomer is selected from dsRNA, siRNA, and shRNA.

7. The method of claim 3, wherein the vesicle is an exosome.

8. The method of claim 1, wherein the administration of the PUM1 inhibitor induces upregulated expressions of interferon and interferon stimulated genes.

9. The method of claim 8, wherein the interferon stimulated genes is selected from LGP2, CXCL10, IL6, PKR, RIG-I, MADS, SP100, IFIT1, PML and STING.

10. The method of claim 1, wherein the subject is a mammal.

11. The method of claim 10, wherein the mammal is a human being.

12. The method of claim 1, wherein the antisense oligomer comprises the sequence of 5'-gcugcuuacuaugac-caaatt-3' (SEQ ID NO: 1).

13. The method of claim 1, wherein the virus is an interferon β sensitive virus.

* * * * *

```
                              SEQUENCE LISTING

<160> NUMBER OF SEQ ID NOS: 43

<210> SEQ ID NO 1
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is t

<400> SEQUENCE: 1
gcugcuuacu augaccaaan n                                                   21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is t

<400> SEQUENCE: 2
ggagauugcu ggacauauan n                                                   21

<210> SEQ ID NO 3
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is t

<400> SEQUENCE: 3
uucuccgaac gugucacgun n                                                   21

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
gagccagtac ctagaactta aac                                                 23

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
```
atggccccat cgagtttg                                                    18

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
acgtgttgag atcattgcta c                                                21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
atcttttaga cctttccttg c                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gccactcacc tcttcagaac g                                                21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
cagtgcctct ttgctgcttt c                                                21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
ggaaagcgaa caaggagtaa g                                                21

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
atcccgtagg tctgtgaaaa ac                                               22

<210> SEQ ID NO 12
<211> LENGTH: 23
<212> TYPE: DNA

```
<213> ORGANISM: Artificial Sequence
<220> FEATURE:
<223> OTHER INFORMATION: Synthetic

<400> SEQUENCE: 12
agaagagtac cacttaaacc cag                                              23

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ttgccacgtc cagtcaatat g                                                21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
ttttcgcctc agaaccgtat t                                                21

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
ctgcacaaac ccttctactc g                                                21

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
aggagtcaaa gcccaccatc                                                  20

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
gtgacgagac cataacggat aac                                              23

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
caaccaagca aatgtgag                                                    18
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aggggaagca agaaaatgg                                                      20

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
cacccgcaag accaacaaca tc                                                  22

<210> SEQ ID NO 21
<211> LENGTH: 23
<212> TYPE: DNA
<213> ORGANISM: Artificial Sequence
<220> FEATURE:
<223> OTHER INFORMATION: Synthetic

<400> SEQUENCE: 21
gcttggaaca tcctcggcag tag                                                 23

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
tcagcattac aacaacctgc tac                                                 23

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
ttatccagga agcgaatgtt g                                                   21

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
tcaagaacaa ggagaagggc aaag                                                24

<210> SEQ ID NO 25
<211> LENGTH: 22
<212> TYPE: DNA
<213> ORGANISM: Artificial Sequence
<220> FEATURE:
```

<223> OTHER INFORMATION: Synthetic

<400> SEQUENCE: 25
tcccgtacca gtagcgaggg tc                                    22

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
taaagccccc aatgcatcca ac                                    22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
ccaaatcctt cccagactcc ac                                    22

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
agagtcaccc atctcagcaa g                                     21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
caccaggacc atcagtaaag c                                     21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ttgtgcttct ccactacagc                                       20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ctgtaagtct gttaatgaag                                       20

```
<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
atgtccaacg caaagcaata c                                              21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gctcttcgac ctcgaaacag                                                20

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
tcatgcacga ccccttttgg                                                19

<210> SEQ ID NO 35
<211> LENGTH: 16
<212> TYPE: DNA
<213> ORGANISM: Artificial Sequence
<220> FEATURE:
<223> OTHER INFORMATION: Synthetic

<400> SEQUENCE: 35
cttggcccgc caacac                                                    16

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gcctgaaaca cacggtcgtt                                                20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
atggtcgtgt tggggttgag                                                20

<210> SEQ ID NO 38
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 38
tttctcctga aacccagaa gatttg                                           26

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
agtcctggct gtctgttggc tc                                              22

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ctcgaagtcg gccatatcca                                                 20

<210> SEQ ID NO 41
<211> LENGTH: 18
<212> TYPE: DNA
<213> ORGANISM: Artificial Sequence
<220> FEATURE:
<223> OTHER INFORMATION: Synthetic

<400> SEQUENCE: 41
ccgggtccgg gatttacc                                                   18

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
ctcaacacgg gaaacctcac                                                 20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
cgctccacca actaagaacg                                                 20
```